United States Patent
Kura et al.

[11] Patent Number: 5,951,289
[45] Date of Patent: Sep. 14, 1999

[54] ARTIFICIAL POSTERIOR TOOTH FOR THE HUMAN TEETH

[76] Inventors: Günter Kura, Römerstr. 54, Bergheim, Germany, 50127; Wilheim Homberg, Reichsstralle 42, Wuppertal, Germany, 42275

[21] Appl. No.: 08/793,840
[22] PCT Filed: Sep. 8, 1995
[86] PCT No.: PCT/EP95/03550
 § 371 Date: May 5, 1997
 § 102(e) Date: May 5, 1997
[87] PCT Pub. No.: WO96/07365
 PCT Pub. Date: Mar. 14, 1996

[30] Foreign Application Priority Data

Sep. 9, 1994 [DE] Germany ............... 44 32 176

[51] Int. Cl.[6] ................................................ A61C 13/08
[52] U.S. Cl. ................ 433/202.1; 433/197; 433/198
[58] Field of Search ................... 433/197, 198, 433/202.1

[56] References Cited

U.S. PATENT DOCUMENTS

| | | | |
|---|---|---|---|
| 2,072,127 | 3/1937 | Pilkington et al. | 433/197 |
| 2,548,956 | 4/1951 | Dickson | 433/197 |
| 3,755,898 | 9/1973 | Warren | 433/197 |
| 4,226,592 | 10/1980 | Schreinemahers | 433/197 |
| 5,501,598 | 3/1996 | Misch | 433/197 |

*Primary Examiner*—Nicholas D. Lucchesi
*Attorney, Agent, or Firm*—Jones & Askew

[57] ABSTRACT

The present invention concerns an artificial posterior tooth, namely a large and small posterior tooth for the upper and lower human jaw, the occlusal surface of which has at least one buccal cusp 6 and at least one palatal cusp 5, between which a longitudinal fissure 7 runs in the longitudinal direction of the tooth, the buccal cusp 6 of the posterior teeth of the lower jaw engaging in the fissure in the posterior teeth of the upper jaw and the palatal cusp 5 of the posterior teeth of the upper jaw engaging in the longitudinal fissure in the posterior teeth of the lower jaw. The longitudinal fissures 7 and the palatal/lingual cusps 5 and buccal cusps 6, respectively, of the posterior teeth 34 to 37 and 24 to 27 are adapted to one another such that, in the region of the longitudinal fissures 7, at least one rest zone 11 is formed in which there is a punctiform contact in the closed position of the posterior teeth 34 to 37 and 24 to 27, respectively.

14 Claims, 9 Drawing Sheets

ARTIFICIAL POSTERIOR TOOTH FOR THE HUMAN TEETH

FIELD OF THE INVENTION

The present invention concerns an artificial posterior tooth, namely a large or small posterior tooth for the upper and lower human jaw, the occlusal surface of which has at least one buccal cusp and at least one palatal or lingual cusp, respectively, between which a longitudinal fissure runs in the longitudinal direction of the tooth, the buccal cusp of the posterior teeth of the lower jaw engaging in the fissusre in the posterior teeth of the upper jaw and the palatal cusp of the posterior teeth or the upper jaw engaging in the longitudinal fissure in the posterior teeth of the lower jaw.

BACKGROUND OF THE INVENTION

Artificial posterior teeth of this type are known. In the case of industrially produced artificial posterior teeth, however, the occlusal surface is only poorly developed and in the closed position a planiform contact region is present between the teeth lying on top of one another. This results in a stamp-like action of the teeth against one another, causing the teeth to adhere during mastication. This adhesion between the teeth leads to poor masticatory properties of the denture formed front the artificial teeth, with the occurrence, in particular, of the so-called "teeth chattering" during mastication. Moreover, in the case of the known artificial, industrially produced teeth, the occlusal surfaces do not interlock satisfactorily As a result, a manual finishing operation is always necessary. Also, the planiform contact region in the closed position of the teeth leads to unfavourable loading of the periodontium.

The object of the present invention is to improve artificial posterior teeth of the type described at the outset such that the masticatory properties and the support in the inserted state are improved and also favourable force distribution in the periodontium is achieved. In addition, the intention is to obtain a simplified alignment of the teeth for the production of the artificial denture.

SUMMARY OF THE INVENTION

The present object is essentially achieved in that the longitudinal fissures and the palatal/lingual cusps and buccal cusps, respectively, of the posterior teeth are adapted to one another such that, in the region of the longitudinal fissures, at least one rest zone is formed in which there is a punctiform contact in the closed position of the posterior teeth. Through the production of a punctiform contact in conjunction with the existing furrowed cusp structure, a stamping action is avoided, as a result of which improved masticatory properties are achieved. Arranging, according to the invention, the rest zones on the longitudinal axis of the teeth leads to the force transmission also being on the longitudinal axis of the teeth, as a result of which the periodontium is spared undue stress. In the case of the prostheses produced using the posterior tooth according to the invention, the dynamics are thus enhanced and the masticatory mechanism relieved since, in an advantageous manner, the rest zones are formed over a wide area.

Furthermore, the present invention consists in forming in each case one or more food discharge grooves in the occlusal surface of the teeth, which grooves lead to the outside via the edge of the respective tooth body. It is particularly expedient here if the food discharge grooves start in the rest zones, at the deepest point thereof. Nevertheless, the formation of food discharge grooves is also expedient without the presence of rest zones. Food discharge grooves of this type are not present in the case of the known artificial teeth, rather the latter merely have faint traces of grooves which are not suitable for carrying off the mashed food resulting during mastication to the outside. By means of the food discharge grooves according to the invention, uniform disintegration of the food is achieved and there is no accumulation and no instability. Moreover, the periodontium is thereby spared undue stress.

A further aspect of the present invention consists in forming positive-locking elements on the opposite lateral surfaces of the posterior teeth, which positive-locking elements correspond in a positive-looking manner with the respectively opposite positive-locking elements of the neighbouring tooth. This brings about an interlocking of the posterior teeth with respect to one another which makes it possible to construct the lower or upper jaw comprising artificial posterior teeth more easily, in denture production. Moreover, an unambiguous assignment and precise alignment of the teeth with respect to one another thereby results. In addition, the interlocking elements serve for mutual support and force transmission. The formation of the interlocking elements on the lateral surfaces is also independent of the occlusal surface being designed with rest zones and/or with food discharge grooves.

By means of the masticatory-surface design according to the invention, it is possible to use the posterior teeth with their interlocking system in a number of ways. The masticatory-surface relief according to the invention allows the function of the posterior teeth with their cusps, rest zones and food discharge grooves to form a unit [sic]. As a result of this system, the tooth according to the invention has multifunctional usability. In this regard, the concept according to the invention allows teeth to occlude individually with respect to one another or to occlude in each case with two teeth, upon interdigitation of the teeth.

Advantageous embodiments of the invention are contained in the subclaims. The invention is explained in greater detail with the aid of the exemplary embodiments illustrated in the accompanying drawings, in which:

FIG. 1 shows a plan view of the occlusal surface of the posterior teeth of the upper jaw, FIG. 2 shows a plan view of the occlusal surface of the posterior teeth of the lower jaw, FIG. 3 shows a buccal view of the teeth according to FIG. 1, FIG. 4 shows a palatal view of the posterior teeth according to FIG. 1, FIG. 5 shows a lingual view of the posterior teeth according to FIG. 2, FIG. 6 shows a buccal view of the posterior teeth according to FIG. 2, FIG. 7 shows a lingual view of the posterior teeth according to FIG. 1 and FIG. 2 in the closed position in an arrangement according to the invention, FIG. 8 a shows a lingual view of the posterior teeth according to FIG. 1 and FIG. 2 in a second arrangement according to the invention, FIG. 9 shows a section through a posterior tooth (24) in the region of the rest zones and FIG. 10 shows a view of a rest zone region.

DETAILED DESCRIPTION OF PREFERRED EMBODIMENTS

Figure 1:
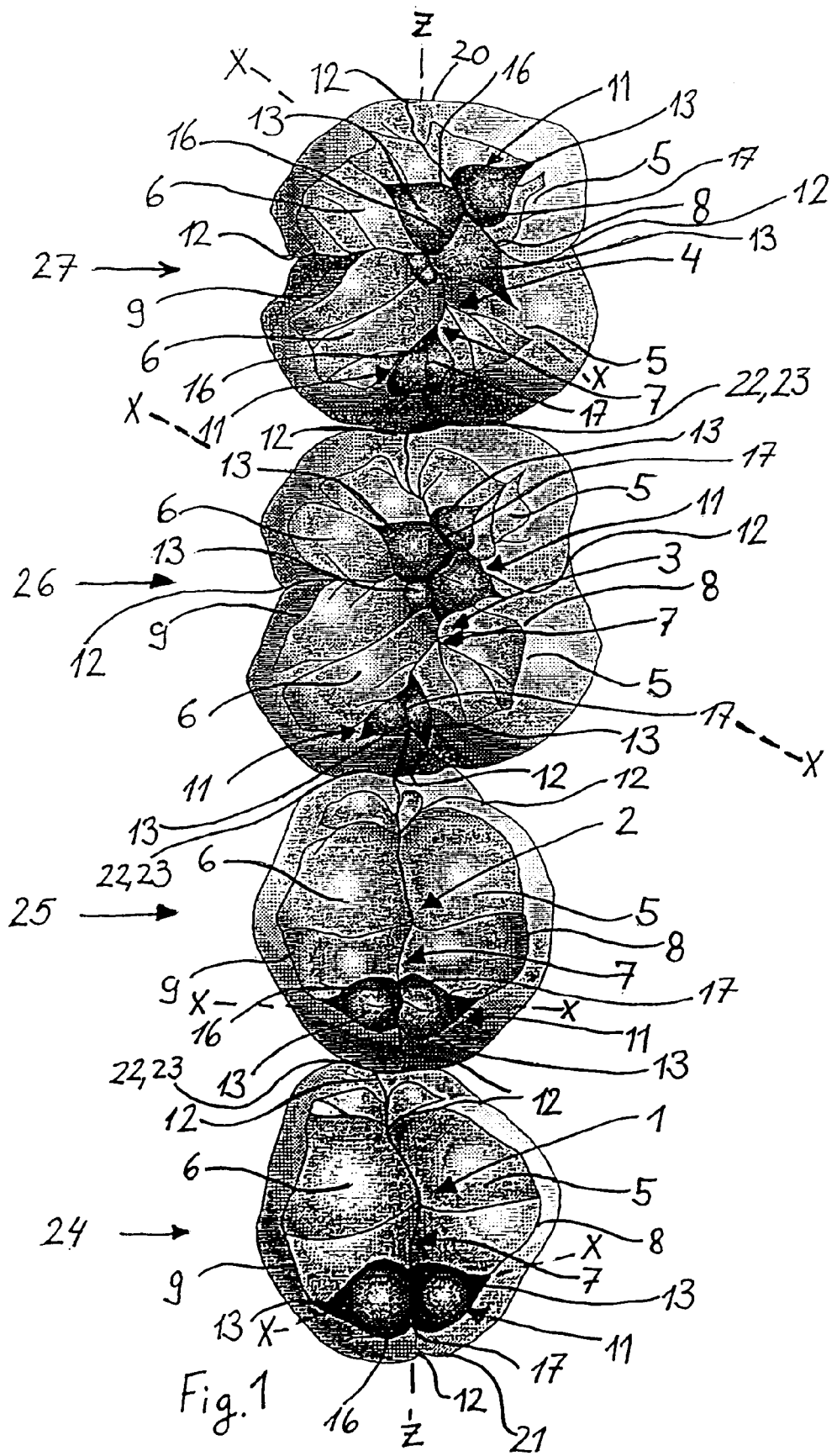

In FIG. 1 the plan view of the small and large posterior teeth of the upper jaw in the second quadrant, that is to say the small posterior teeth 24, 25 and the large posterior teeth 26, 27 of the upper jaw, is illustrated The numbering shown corresponds to the numbering which is customary in dentistry for numbering the teeth of the upper and lower jaw. Thus, in each case the occlusal surface of each individual tooth can be seen in this FIG. 1. Each of the large and small posterior teeth has, in its occlusal surface 1, 2, 3, 4, at least one or two palatal cusps 5, respectively, and at least one or two buccal cusps 6, respectively. The small posterior teeth 24, 25 preferably possess two cusps 5, 6 each. The large posterior teeth 26, 27 possess buccally two approximately equal-sized cusps 6 and palatally one large cusp 5 which is mesial and on e smaller cusp 5 which is distal. Between the palatal cusps 5 and the buccal cusps 6 there is formed a longitudinal fissure (furrow) 7. In FIG. 1 the reference numeral 8 denotes the palatal tooth ridge and the reference nuneral 9 denotes the buccaal tooth ridge. According to the invention, rest zones 11 are formed within the longitudinal fissure 7 in each of the teeth 24, 25, 26, 27. The distinctive feature of these rest zones 11 is that the supporting cusps of the antagonist (the opposing tooth of the lower jaw), that is to say the buccal cusps of the lower jaw, see FIG. 6, bear in these rest zones with point contact in the closed position of the upper and lower jaw and in the remaining region of the occlusal surfaces 1, 2, 3, 4 there is no touching contact.

Figure 9:
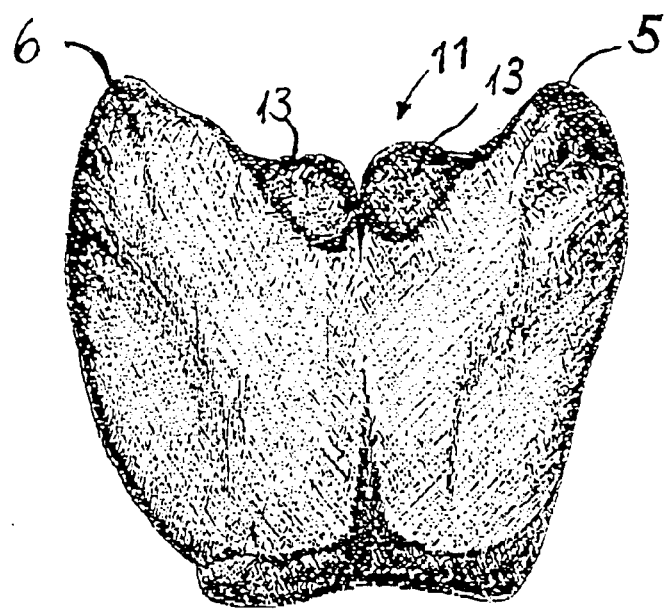
Figure 10:
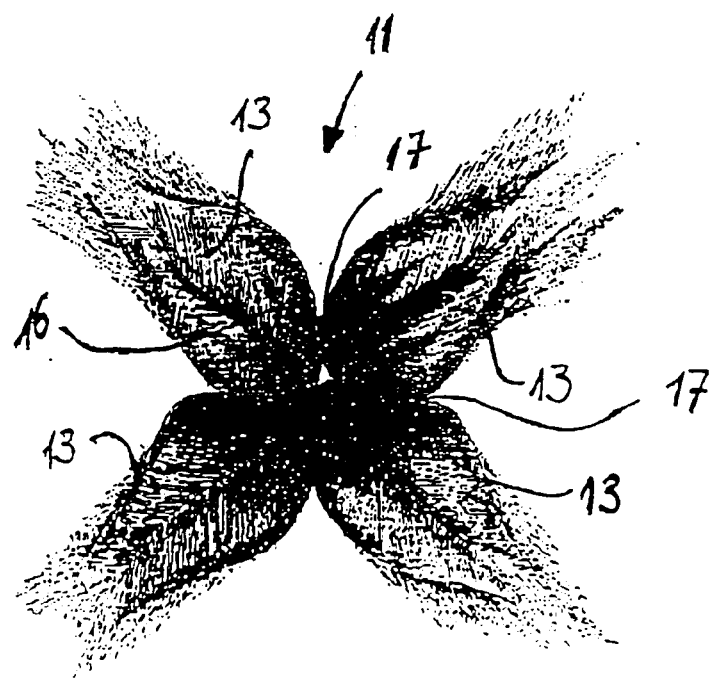

The rest zones 11 each have a plurality of contact regions 13, it being possible for there to be a point contact on the cusps of the antagonist in each contact region in the closed position The contact regions 13 have approximately the outline contour of an onion, i.e. they possess a bulbous central region 14 adjoined by a tapering top region 15. The surface of the contact regions 13 is toroidal-shaped, and, seen in cross-section both in the longitudinal direction X—X and in the Y—Y direction perpendicular thereto, a convex sectional contour is formed. In FIG. 9 an individual contact region is illustrated. The contact regions 13 butt against one another by the base 16 of the central region 14, so that between them fissures 17 are formed which run out towards the tooth edge.

The supporting cusps of the antagonist thus find support over a wide area in the rest zone, i.e. a corresponding clearance is present around the punctiform contact region. As a result, the entire masticatory mechanism is relieved and sufficient freedom is thereby brought about in the region of the posterior teeth on all excursions of the lower jaw. In order to ensure this punctiforn contact, a furrowed cusp structure is present according to the invention, the cusps being convex-shaped. As is revealed in FIG. 1, these rest zones 11 are formed differently in terms of size and position in the individual posterior teeth 24 to 27. In the case of the two small posterior teeth 24, 25, in each case merely one rest zone 11 is provided which is preferably situated in the mesial ridge region of the tooth. This rest zone 11 comprises two contact regions 13 which are arranged in such a way that the longitudinal axis X—X runs somewhat perpendicular to the longitudinal fissure 7. The two large posterior teeth 26, 27 have two rest zones 11 which are spaced in the longitudinal direction, one smaller rest zone 11 being located in the mesial ridge region and one larger rest zone 11 being offset distally with respect to the tooth centre. Here, the larger rest zone 11 comprises four contact regions 13, three of which are approximately equal-sized and larger than the fourth contact region. The four contact regions 13 are arranged in the shape of a star, the longitudinal axes X—X of the two respectively mutually opposite contact regions 13 running obliquely with respect to the longitudinal fissure 7, and the smaller contact region 13 being located approximately in the tooth centre. The small rest zone 11 comprises two contact regions 13 which are arranged approximately in correspondence with that of the premolars but have smaller dimensions than these. The smaller rest zones 11 have about a width of approximately 0.17 cm, and the larger rest zones 11 have about a width of approximately 0.24 cm.

Figure 2:
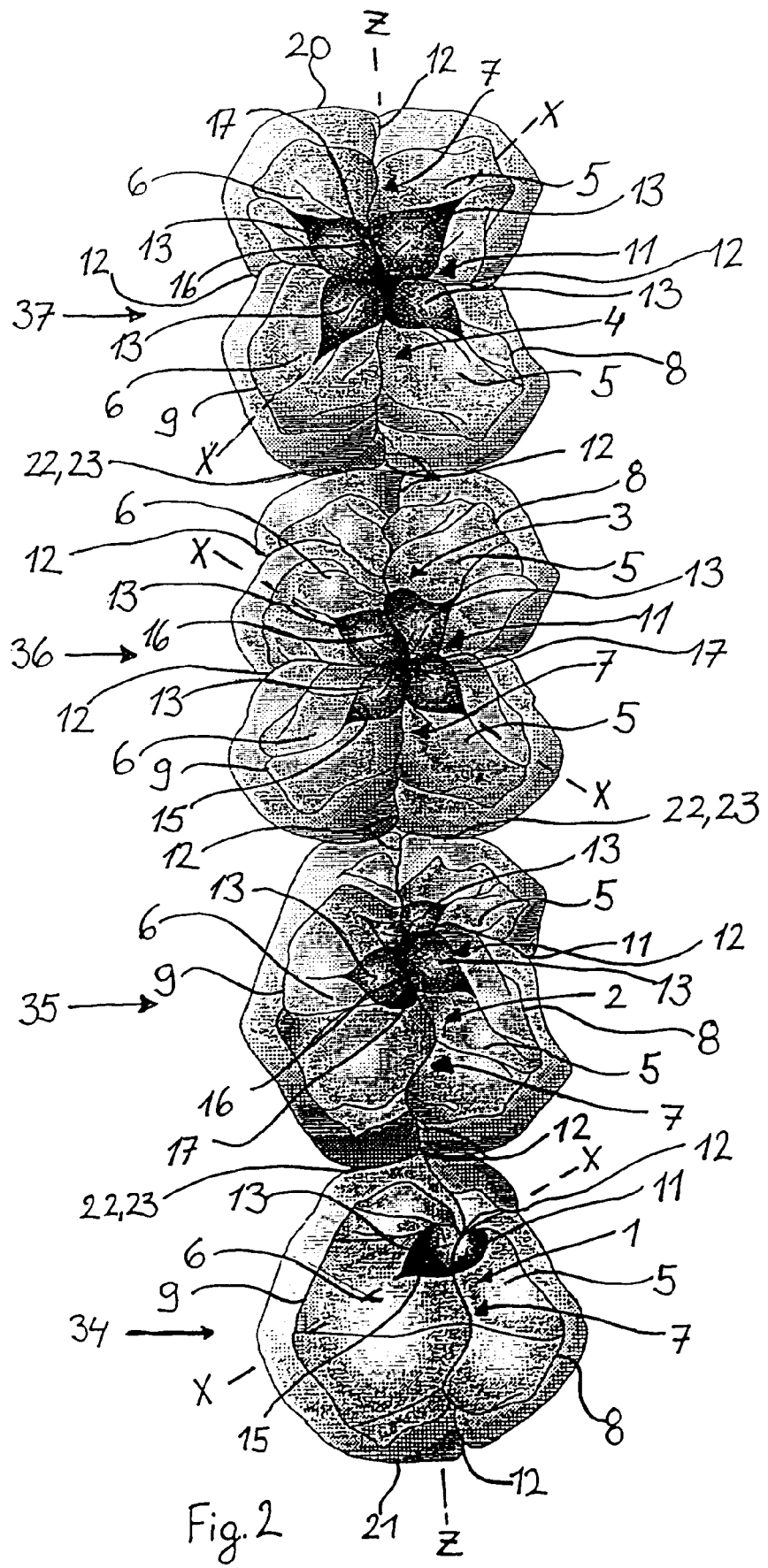

In FIG. 2 the small posterior teeth 34, 35 and the large posterior teeth 36, 37 in the third quadrant of the lower human jaw are illustrated, the numbering of the teeth again corresponding, in this case too, to the numbering of the teeth of the lower jaw which is customary in dentistry. In FIG. 2, identical tooth features to those in FIG. 1 are given the same reference numerals As already stated, in the case of the teeth 34 to 37 of the lower jaw, the buccal cusps 6 form the occlusion-fixing cusps and engage in the longitudinal fissure 7 in the respective antagonists of the upper jaw. In contrast, the occlusion-fixing palatal cusps 5 of the teeth 24 to 27 of the upper jaw engage in the longitudinal fissure 7 in their respective antagonist in the lower jaw.

As is evident from FIG. 2, in each case one rest zone 11 is formed in the teeth 34 to 37 of the lower jaw. Here, the rest zones 11 in the small posterior teeth 34, 35 are situated in the distal region, whereas the rest zones 11 in the large posterior teeth 36, 37 are formed approximately in the tooth centre in the occlusal surface of the teeth 36, 37, In the case of the teeth 34 to 37 of the lower jaw, too, the lingual cusps 5 and the buccal cusps 6 are convex-shaped. The flank angle of the cusps 5, 6 is 20 to 30° here, thus ensuring a punctiform contact in the respective antagonist in the region of the longitudinal fissure 7 and there in the respective contact regions 13.

The small posterior teeth 34, 35 are preferably formed in such a way that the posterior tooth 34 has two cusps 5, 6 and the posterior tooth 35 has three cusps, namely one buccal cusp 6 and two lingual cusps 5. The rest zone 11 of the posterior tooth 34 comprises a contact region 13 in the distal masticatory-surface region, the top region 15 pointing in the buccal direction. The posterior region 35 possesses a rest zone 11 comprising four contact regions 13 arranged approximately in the shape of a star, namely two smaller distally adjacent contact regions, which bear by their base 16 in each case against the base 16 of two larger contact regions, the top region 15 of which is directed approximately buccally and lingually, respectively, and this also applies to the top regions 15 of the smaller contact regions 13. The large posterior teeth 36, 37 possess buccally two approximately equal-sized cusps 6, or three different-sized cusps, and lingually two equal-sized or different-sized cusps 5. The rest zones 11 of both posterior teeth 36, 37 are arranged approximately in the tooth centre, the four contact regions 13 being arranged approximately in the shape of a star and their longitudinal axes X—X running obliquely with respect to the longitudinal fissure 7.

The rest zones 11 are each arranged approximately on the longitudinal axis Z—Z of the teeth. That is to say the longitudinal fissure 7 divides approximately centrically in each case the individual posterior teeth 24 to 27 and 34 to 37 of the upper jaw and lower jaw, respectively. A uniform masticatory pressure on the longitudinal axis of the teeth is thereby achieved, the result of which is that the dynamics during mastication are improved and the periodontium is spared undue stress .

In the region of the premolars, the rest zones 11 have an extent both in the longitudinal direction and in the transverse direction of approximately 0.17 cm and in the region of the molars they have a maximum extent in the longitudinal direction and in the transverse direction of approximately 0.24 cm.

Furthermore, it may also be expedient, according to the invention, if the rest zones 11 are formed in such a way that they extend over the entire region of the longitudinal fissures 7 in the individual teeth 24 to 27 and 34 to 37. In this case, the occlusion-fixing cusps, i.e. the buccal cusps 6 of the posterior teeth 34, 37 of the lower jaw and the palatal cusps 5 of the posterior teeth 24 to 27 of the upper jaw, are saddle-shaped in the region of their ridges.

A further expedient development of the invention, which is also independent of the formation of the rest zones described in FIGS. 1 and 2, consists in forming in the region of the respective longitudinal fissure 7 in the individual teeth 24 to 27 and 34 to 37; respectively, discharge grooves 12 which lead to the outside via the edge of the tooth body of the respective tooth. These discharge grooves 12 start, insofar as rest zones 11, according to the invenotion, are present, at the deepest point of the respective rest zone 11. These discharge grooves 12 are approximately V-shaped in cross-section and have in each case a depth of about 0.27 mm in the premolars 24, 25 and 34, 35 and a depth of approximately 0.40 mm in the molars 26, 27 and 36, 37. This depth is present in particular at the start of the discharge groove 12 in the region of the rest zone. At the end of the discharge groove 12 in the wall region of the tooth body, the discharge groove 12 runs out at a depth "0". As is evident from FIGS. 1 and 2, in the case of the small. posterior teeth (premolars) 24, 25 arod 34, 35, respectively, in each case at least one discharge groove 12 is formed in such a way that it starts in the respective rest zone 11 and runs out in the lingual and palatal wall region of the tooth body, respectively, and in each case one discharge groove 12 runs out of the longitudinal fissure 7 into the wall region of the two lateral surfaces. In the case of the large posterior teeth (molars) 36, 37 and 26, 27, respectively, at least two discharge grooves 12 are provided, one running out in the palatal/lingual wall and the other in the buccal wall of the respective tooth body, and in each case one discharge groove 12 runs out of the longitudinal fissure 7 into the wall region of the two lateral surfaces. The discharge grooves 12 according to the invention ensure that the food which is comminuted on the masticatory surfaces is forced out of the masticatory surface in the closed position of the teeth, so that the mashed food is able to flow off and thus mutual adhesion of the teeth in the region of their masticatory surfaces caused by the mashed food is avoided. Moreover, an accumulation of food is prevented and thus instabilities are avoided.

It can be seen furthermore from FIGS. 1 and 2 that there is provision according to the invention, and again independently of the formation of the rest zones 11 and the food discharge grooves 12, in each case for positive-locking elements 22, 23 to be formed on the lateral surfaces 20, 21 of the individual teeth, which positive-locking elements are shaped in such a way that respectively opposite positive-locking elements of neighbouring teeth correspond in a positive-locking manner with one another, in particular with linear contact. The positive-locking elements may be convex projections of one tooth and correspondingly adapted concave indentations of the other tooth. As a result, an interlocking of the teeth with one another is achieved. By means of this interlocking, the teeth are aligned with respect to one another and at the same time are better supported against one another.

Figure 3:
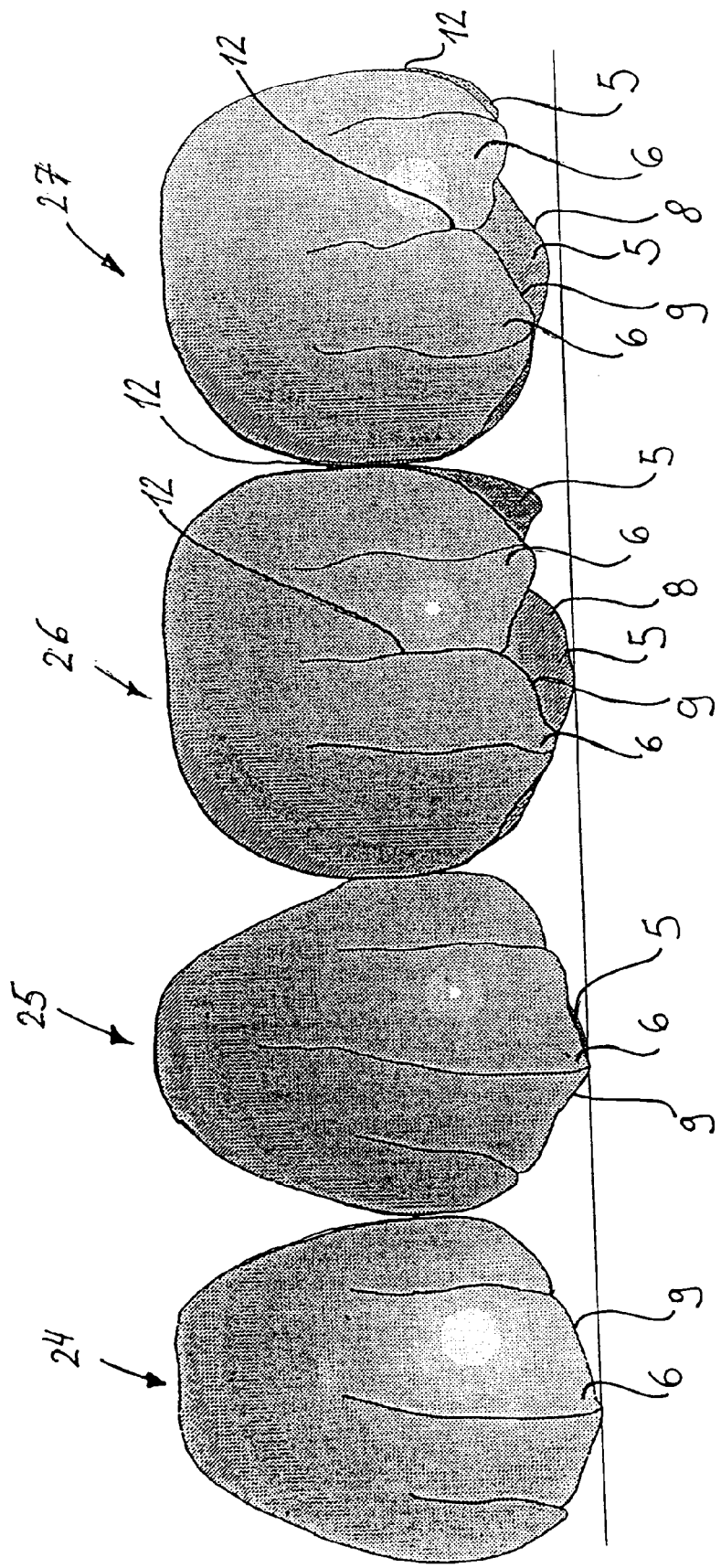

In FIG. 3 a buccal view of the teeth 24 to 27 is illustrated.

Figure 4:
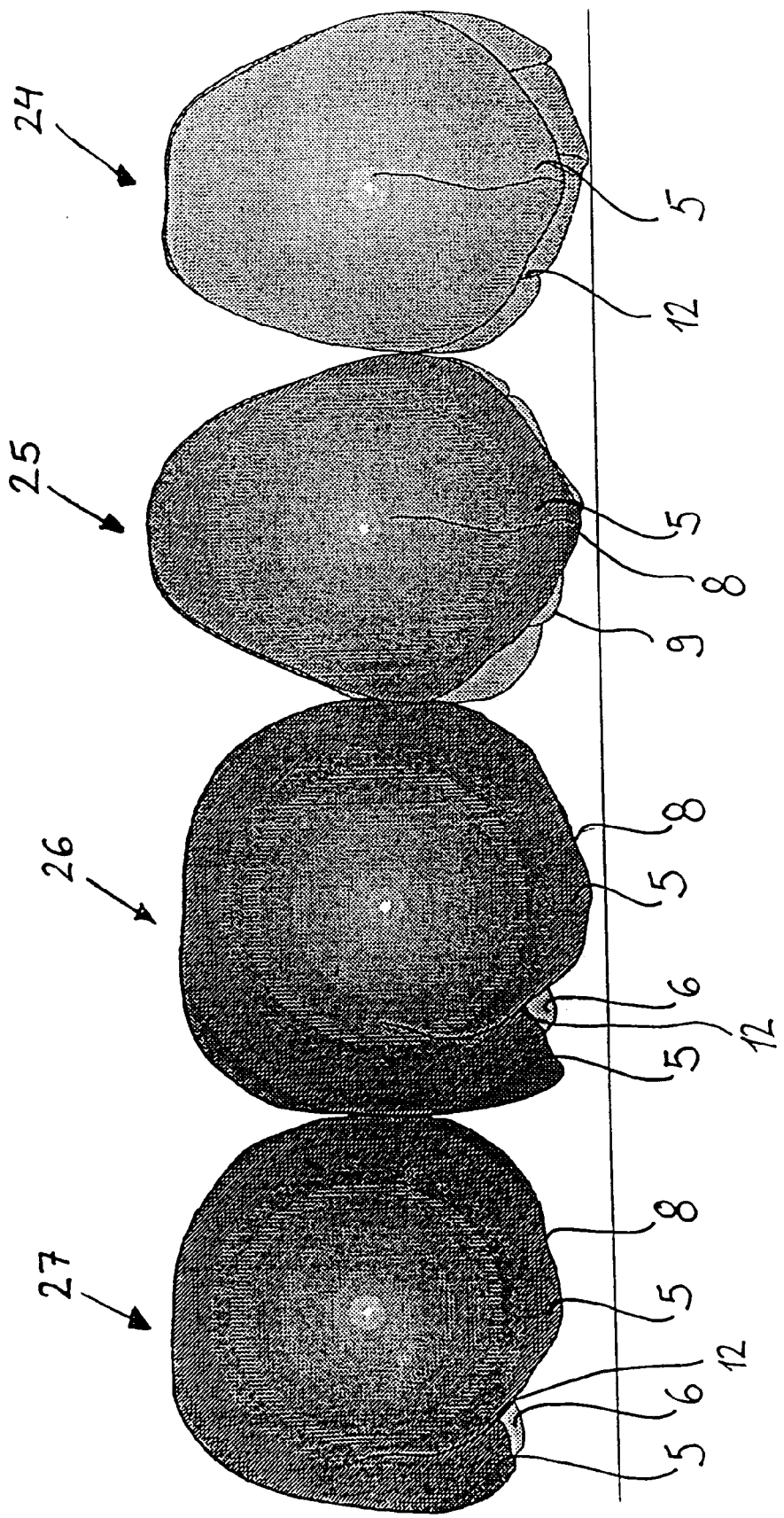

FIG. 4 shows the palatal view, associated with the buccal view according to FIG. 3, of the teeth 24 to 27. In these figures, identical tooth portions to those in FIGS. 1 and 2 are given the same reference numerals.

Figure 5:
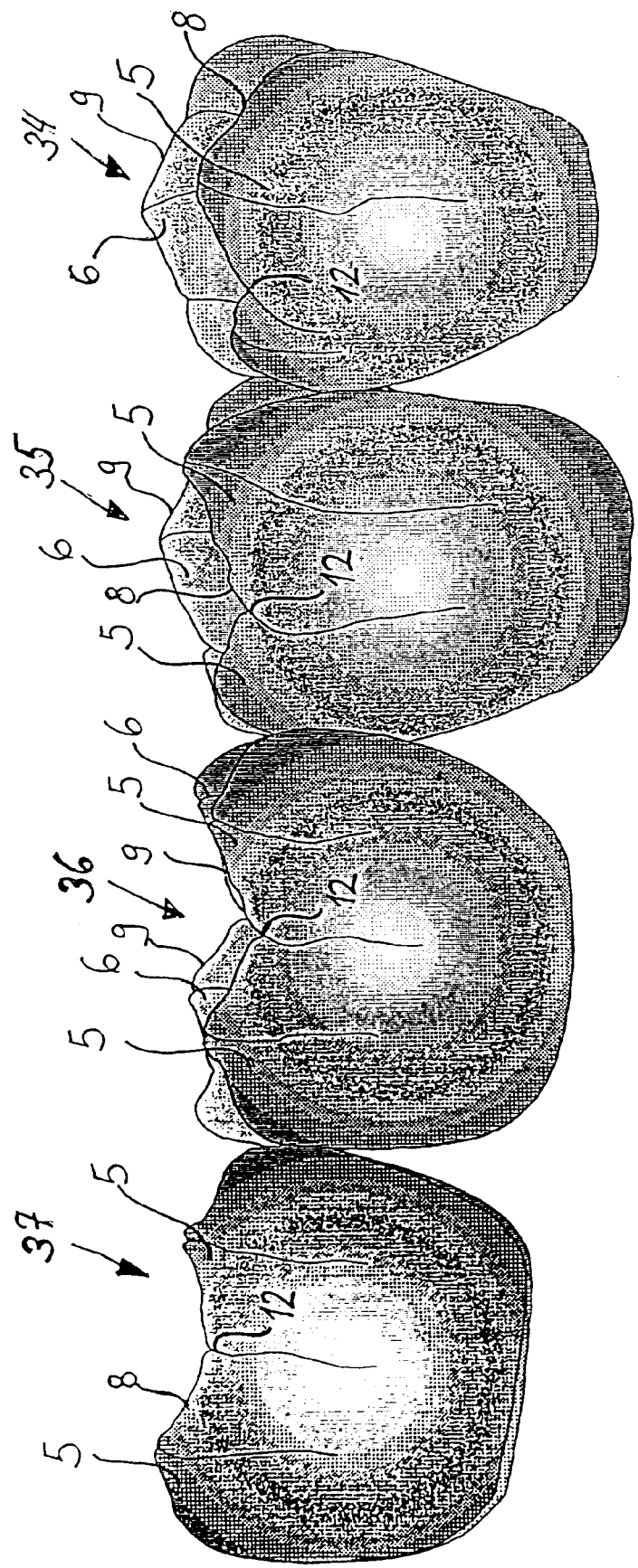
Figure 6:
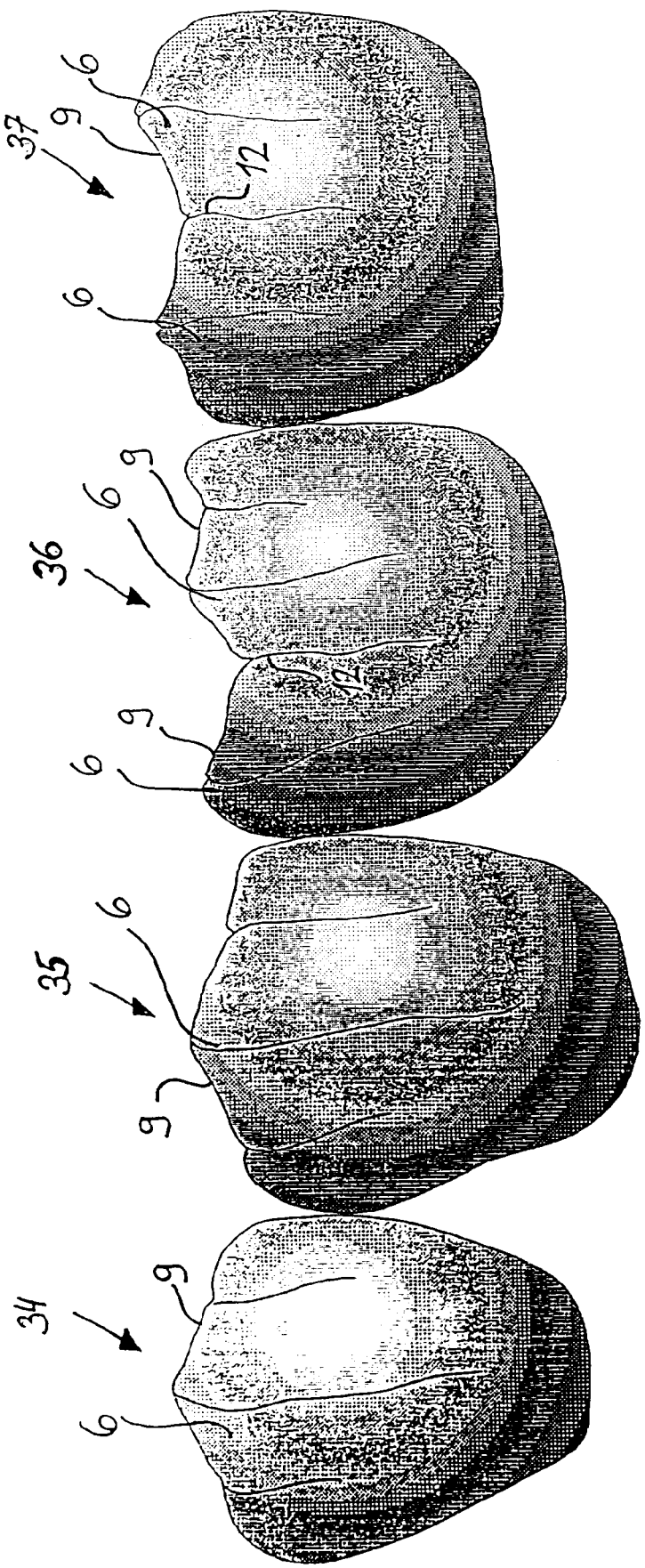

In FIG. 5 the lingual view of the teeth 34 to 37 is illustrated. FIG. 6 shows the buccal view, associated therewith, of the teeth 34 to 37, identical tooth portions to those in FIG. 2 again being given the same reference numerals.

Figure 7:
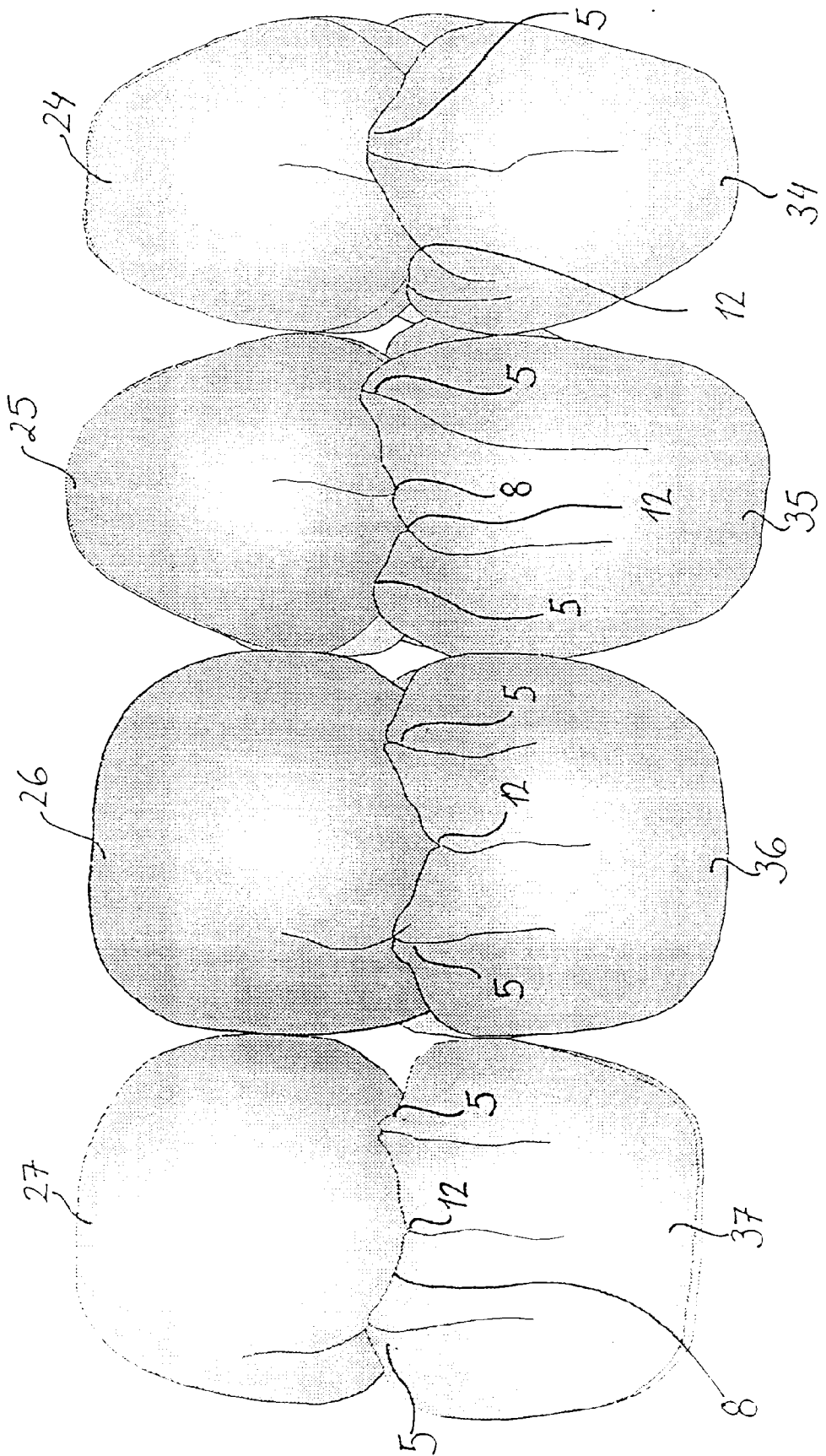
Figure 8:
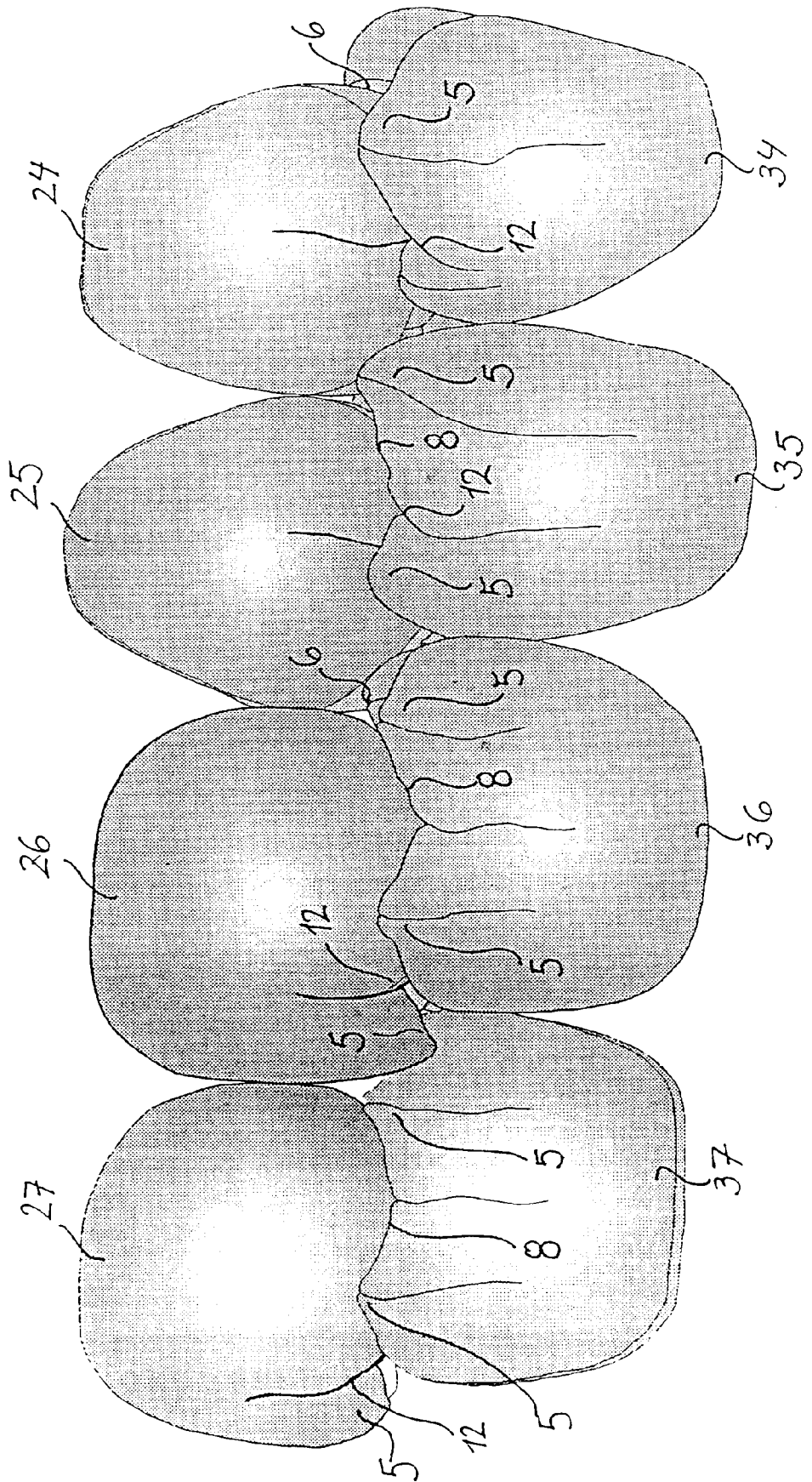

In FIG. 7 the lingual view in the closed position of the teeth 34 to 37 and 24 to 27 is illustrated. Here, it can be seen that the teeth can be arranged in a so-called one-to-one tooth relationship. FIG. 8 likewise shows the lingual view of the teeth 24 to 27 and 34 to 37, respectively, in the closed position. here, however, a so-called one-to-two tooth relationship is illustrated. By means of the design, according to the invention, of the occlusal surfaces 1 to 4 of the small and large posterior teeth, it is possible to construct both a one-to-one tooth relationship and a one-to-two tooth relationship.

We claim:

1. A large and small artificial posterior tooth pair for the human upper and lower jaw, the occlusal surfaces of which comprise at least one buccal cusp and at least one palatal cusp, between which a longitudinal fissure runs in the longitudinal direction of the tooth, where the buccal cusp of the lower jaw posterior tooth engages in the longitudinal fissure of the upper jaw posterior tooth and the palatal protuberance of the upper jaw posterior tooth engages in the longitudinal fissure of the lower jaw posterior tooth, comprising:

the longitudinal fissures (7) and the palatal/lingual cusp (5) and the buccal cusp (6) of the posterior teeth (34–37, 24–27) are coordinated with each other to form, in the region of the longitudinal fissures (7) that divide the side teeth (24–27, 34–37) approximately in the middle, at least one rest zone (11) in the median longitudinal axis (Z—Z) of the tooth, the rest zone having at least one contact region (13);

supporting cusps of antagonist teeth of said pair lying on the at least one contact region (13) with point contact of occlusal surfaces (1,2,3,4) in the closed position of the upper and lower jaws; and the remaining region of the occlusal surfaces (1,2,3,4) having no touching contact, thereby avoiding a stamping action and improving masticatory properties of the tooth pair.

2. Artificial posterior tooth according to claim 1, characterised by construction as a large posterior tooth (26, 27) of the upper jaw, two rest zones (11) spaced in the longitudinal direction of the posterior tooth (26, 27) being present, one being formed in the distal region and the other in the mesial region.

3. Artificial posterior tooth according to claim 1 characterised by construction as a small posterior tooth (24, 25) of the upper jaw, one rest zone (11) being formed in the mesial region.

4. Artificial posterior tooth according to claim 1, characterised by construction as a large posterior tooth (36, 37) of the lower jaw, one rest zone (11) being formed approximately in the centre of the occlusal surface (3, 4).

5. Artificial posterior tooth according to claim 1, characterised by construction as a small posterior tooth (34, 35) of the lower jaw, one rest zone (11) being provided in the distal region.

6. Artificial tooth according to claim 1, characterised in that the palatal/lingual cusps (5) and the buccal cusps (6) are convex-shaped and in particular have a flank angle of approximately 20 to 30'.

7. Artificial posterior tooth according to claim 1, characterised in that the rest zones (11) extend over the entire length of the longitudinal fissure (7) and the occlution-fixing palatal cusps (5) and the buccal cusps (6) are saddle-roof-shaped in longitudinal section.

8. Artificial posterior tooth according to claim 1, characterised in that an antistress region is formed around the rest zone (11) for enlarging the said rest zone (11).

9. Artificial tooth according to claim 1, characterised in that the rest zones (11) comprise at least one contact portion (13) having a torodal-shaped surface.

10. Artificial posterior tooth, namely, a small posterior tooth and a large posterior tooth for the upper and lower jaw in humans, the occlusal surface of which has at least one buccal cusp and at least one palatal cusp, between which a longitudinal fissure runs in the longitudinal direction of the tooth, in particular according to claim 1, characterised in that at least one food discharge groove (12) leads to the outside via the edge of the respective tooth body, starting from the longitudinal fissure (7).

11. Artificial posterior tooth according to claim 10, characterised in that the at least one food discharge groove (12) starts in the rest zones (11, at the deepest point thereof.

12. Artificial tooth according to claim 10, characterised in that the at least one food discharge groove (12) is v-shaped in a cross-section and preferably has a depth of 0.5 to 0.7 mm at the start of the rest zone (11) and run out towards the end.

13. Artificial posterior tooth, in particular a small or large posterior tooth for the upper jaw and lower jaw in humans, the occlusal surface of which has at least one buccal cusp and at least one palatal cusp, between which a longitudinal fissure runs in the longitudinal direction of the tooth, in particular according to claim 1, characterised in that positive-locking elements (22, 23) are formed on the opposite lateral surfaces (20, 21) of the posterior teeth (24 to 27) and (34 to 37), respectively, which positive-locking elements correspond in a positive-locking manner with their respectively opposite positive-locking elements of the neighbouring tooth.

14. Artificial posterior tooth according to claim 13, characterised in that the positive-locking elements (22, 23) are convex- and concave-shaped, respectively.

* * * * *